US00PP22616P2

(12) United States Plant Patent
Blom

(10) Patent No.: US PP22,616 P2
(45) Date of Patent: Apr. 3, 2012

(54) ***CHRYSANTHEMUM* PLANT NAMED 'ZANMUDENALI'**

(50) Latin Name: ***Chrysanthemum×morifolium* Ramat.**
Varietal Denomination: Zanmudenali

(75) Inventor: Wilhelmus Bernardus Blom, Leimuiden (NL)

(73) Assignee: Chrysanthemum Breeders Association Research B.V., Valkenburg Z-H (NL)

( * ) Notice: Subject to any disclaimer, the term of this patent is extended or adjusted under 35 U.S.C. 154(b) by 0 days.

(21) Appl. No.: 12/923,735

(22) Filed: Oct. 6, 2010

(51) Int. Cl.
*A01H 5/00* (2006.01)

(52) U.S. Cl. ..... Plt./288

(58) Field of Classification Search ..... Plt./288, Plt./294

See application file for complete search history.

*Primary Examiner* — Kent L Bell

(74) *Attorney, Agent, or Firm* — Steptoe & Johnson LLP

(57) ABSTRACT

A *chrysanthemum* plant named 'Zanmudenali' characterized by its large sized blooms with white ray florets and prolific branching, and a response time of 7.5 weeks.

3 Drawing Sheets

Botanical designation: *Chrysanthemum×morifolium* Ramat.

Cultivar denomination: 'Zanmudenali'.

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmudenali'. 'Zanmudenali' is a product of a breeding and selection program for pot mums which had the objective of creating new cultivars with an anemone type inflorescence, a medium plant height and a response time of 7-8 weeks. 'Zanmudenali' is a seedling resulting from a cross of the female parent id 44258 and the male parent id 8967. Plants of the new cultivar 'Zanmudenali' differ from plants of the female parent in the following characteristics: (1) Inflorescence size. The inflorescences of the female parent are smaller than those of the seedling. And (2), Vigor. Plants of the female parent are less vigorous than those of the seedling. Plants of the new cultivar 'Zanmudenali' differ from plants of the male parent in plant vigor; the plants of the male parent are less vigorous.

The new and distinct cultivar was discovered and selected as a flowering plant within the progeny of the stated cross by Wilhelmus Bernardus Blom in a controlled environment (greenhouse) in Rijsenhout, The Netherlands in April 2003. The first act of asexual production of 'Zanmudenali' was accomplished when vegetative cuttings were used from the initial selection in June 2003 and propagated further in a controlled environment in Rijsenhout, The Netherlands. The new cultivar has been found to retain its distinctive characteristics through successive propagations, although the phenotype may somewhat vary with variations in environment such as light intensity and temperature.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
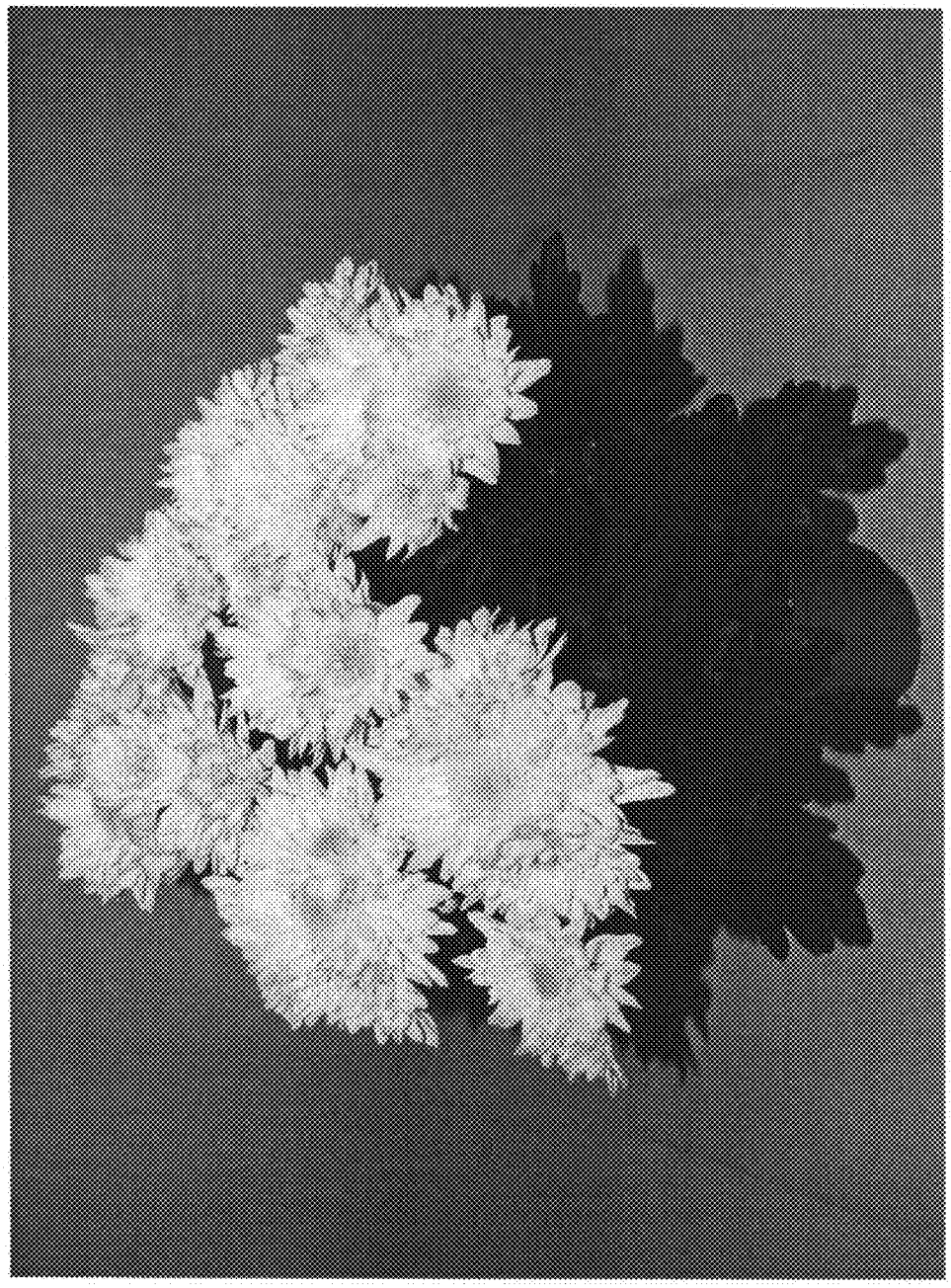
FIG. 1 shows a plant of the cultivar in full bloom.
Figure 2:
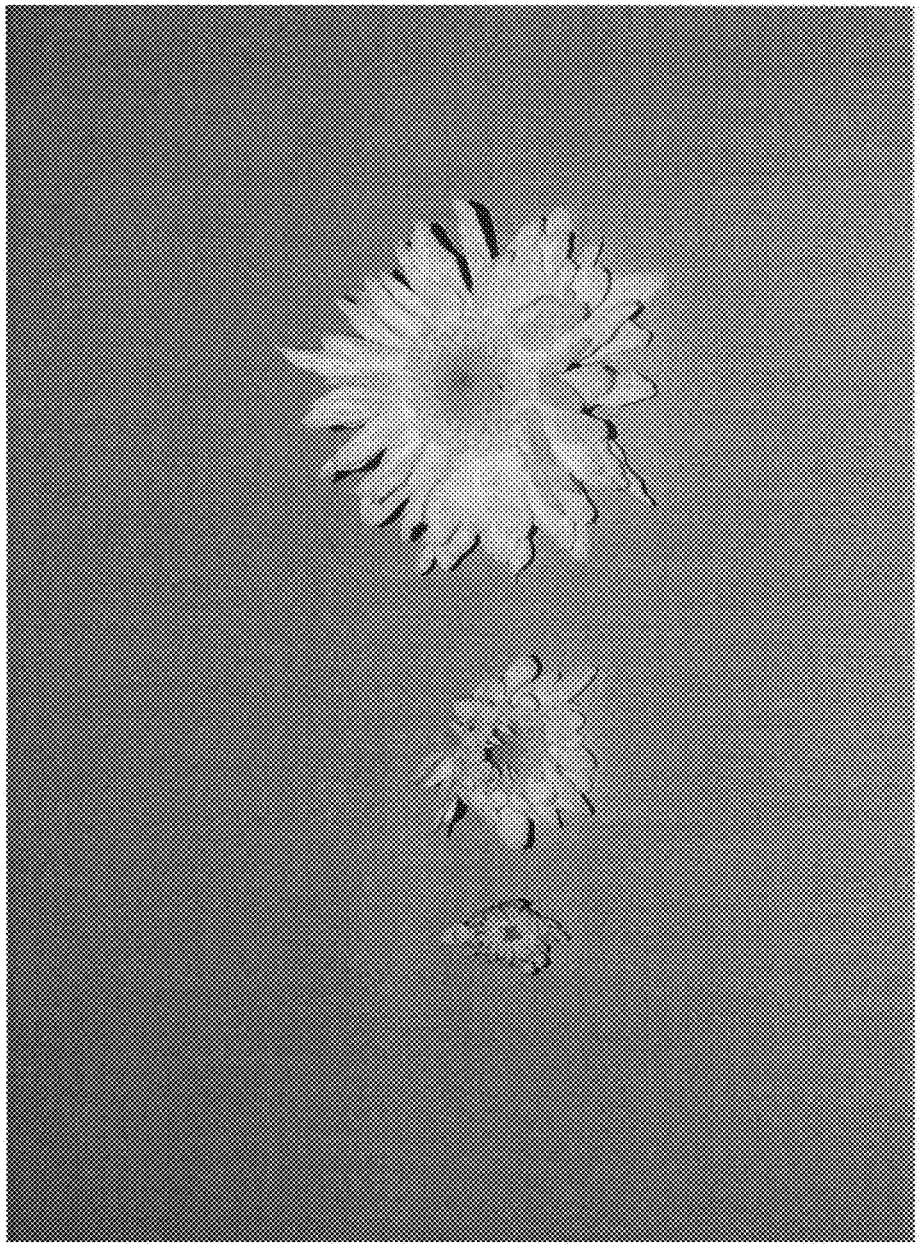
FIG. 2 shows the various stages of bloom of the new cultivar.
Figure 3:
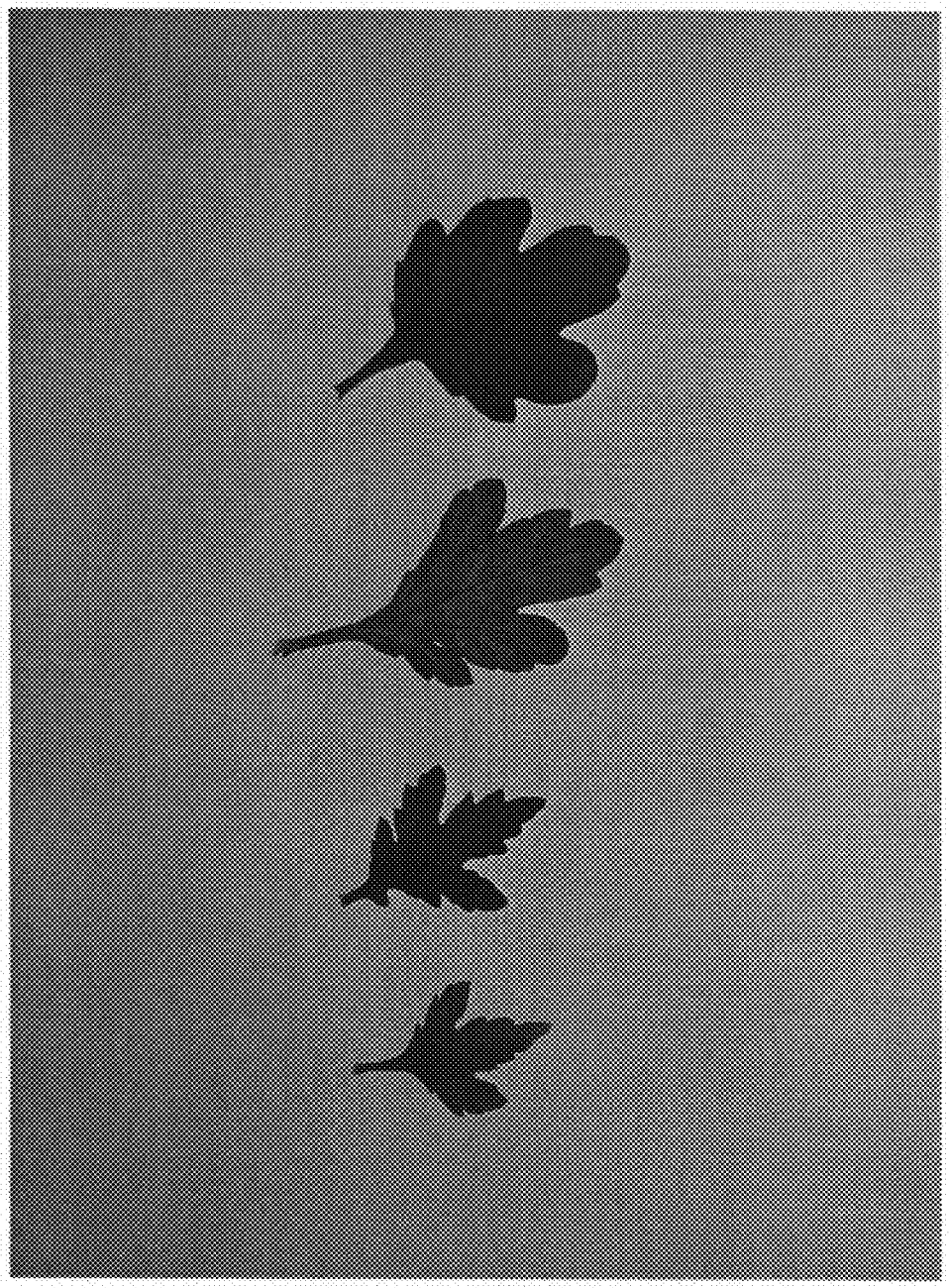
FIG. 3 shows the various stages of foliage of the new cultivar.

The observations and measurements were gathered in May 2010 from plants grown in a controlled environment (greenhouse) in Rijsenhout, The Netherlands, in a photo-periodic controlled crop under conditions generally used in commercial practice. Three cuttings were planted in a pot with a diameter of 12 cm. The greenhouse temperatures for this crop were at daytime 18.degree. C. to 25.degree. C., and at night about 20.degree. C. The photo-periodic response time in this crop was 7.5 weeks after an average of eight long days. After this long day period growth retardants (Alar) were applied six times in an average dose of 1.5 gram/liter water until flowering. The plants were observed (directly) during the flowering of this crop. No tests were done on disease or insect resistance or susceptibility. No tests were done on cold or drought tolerance. To show the phenotype as described 'Zanmudenali' can be planted without assimilation lighting (high pressure sodium lamps) between week 50 and week 40 of the next year under greenhouse conditions in the Netherlands. With assimilation lighting (minimum level 2500 lux) it can be planted all year round under greenhouse conditions in The Netherlands. This new variety produces large sized blooms with white florets and a response time of 7.5 weeks.

From the cultivars known to inventor the most similar existing cultivar in comparison to 'Zanmudenali' is 'Letitia Time Improved' (U.S. Plant Pat. No. 18,359). When 'Letitia Time Improved' and 'Zanmudenali' are being compared the following difference is noticed: The difference of 'Letitia Time Improved' and 'Zanmudenali' are (1) Inflorescence type. And (2) Ray floret color. (1) The inflorescence type in 'Letitia Time Improved' is single, that of 'Zanmudenali' is anemone. (2) The ray-florets of 'Letitia Time Improved' are cream colored, while those of 'Zanmudenali' are white.

The following is a description of the plant and characteristics that distinguish 'Zanmudenali' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum xmorifolium* Ramat. 'Zanmudenali'

| | |
|---|---|
| Bud | |
| Size | Medium; cross-section 7 mm, height 6 mm |
| Shape | Round |
| Texture | Smooth |
| Outside Color | Greyed-green 191A |
| Phyllaries | |
| Number | 26, arranged in 3 rows |
| Shape | Elliptic |
| Apex | Acute |
| Base | Truncate |
| Margin | Entire |
| Color | Upper surface: Greyed-green 191A<br>Lower surface: Greyed-green 191B |
| Length and width | 1-1.5 cm; 2 mm |
| Texture | Pubescent |
| Inflorescence | |
| Type | Anemone |
| Height | 2 cm |
| Diameter | 9 cm |
| Peduncle length | 2.5 cm |
| Peduncle color | Green 139B |
| Peduncle diameter | 2 mm |
| Peduncle texture | Pubescent |
| Number per branch | Approx. 6 inflorescences |
| Shelf life | 4 weeks |
| Seeds | Produced in small quantities, ovate, Greyed-brown 199A, length 1.5 mm, diameter 0.8 mm |
| Fragrance | Faint *chrysanthemum* odor |
| Color | |
| Center of inflorescence (disc florets) | Immature stage: Yellow-green 144C<br>Mature stage: Green-yellow 1D |
| Color of upper surface of the ray-florets | White 155D |
| Color of the lower surface of the ray-florets | White 155D |
| Tonality from Distance | A pot *mum* with large white flowers |
| Color of the upper and lower surfaces of ray-florets after aging of the plant | White 155D |
| Ray florets | |
| Texture | Upper and lower side smooth |
| Number | 76-80 |
| Shape | Elliptic |
| Apex | Dentate |
| Base | Attenuate |
| Cross-section | Flat |
| Longitudinal axis of majority | Twisted |
| Length of corolla tube | 0.4 cm |
| Ray-floret margin | Entire |
| Ray-floret length | 3.5-4 cm |
| Ray-floret width | 2 cm |
| Ratio length/width | Medium |
| Disc florets | |
| Disc diameter | 3 cm |
| Distribution of disc florets | Abundant |

TABLE 1-continued

Botanical Description of *Chrysanthemum xmorifolium* Ramat. 'Zanmudenali'

| | |
|---|---|
| Shape | Funnel |
| Color | White 155D at apex, Yellow 9D at base |
| Length | 1.2 cm |
| Diameter | 0.2 cm |
| Receptacle | |
| Color | Yellow-green 145D |
| Shape | Domed raised |
| Height | 5 mm |
| Diameter | 6 mm |
| Reproductive Organs | |
| Androecium | Present on disc florets only |
| Stamen length | 3 mm |
| Stamen color | Yellow-green 144A |
| Anther color | Yellow 3A |
| Pollen | Present |
| Pollen | Yellow 12A |
| Gynoecium | Present on both ray and disc florets |
| Style color | Yellow-green 154C |
| Style Length | 3 mm |
| Stigma color | Yellow 7A |
| Stigma Width | 1 mm |
| Ovary | Enclosed in calyx |
| Plant | |
| Form | Upright and free branching |
| Growth rate | Medium |
| Height | 20 cm |
| Width | 30 cm |
| Stem Color | Greyed-brown 199A |
| Stem Strength | Strong |
| Stem Brittleness | Not brittle |
| Stem Anthocyanin Coloration | Not observed |
| Internode length | 1-2 cm |
| Length of lateral branch | From top to bottom 9 cm |
| Lateral branch color | Green 137 C |
| Lateral branch diameter | 0.3 cm |
| Lateral branch, attachment | Strong |
| Branching (average number of lateral branches) | Prolific with 4 breaks after pinching |
| Response time | 7.5 weeks |
| Foliage | |
| Leaf color | Upper surface: Green 136A<br>Lower surface: Green 138B |
| Color midvein | Upper surface: Yellow-green 147D<br>Lower surface: Yellow-green 148D |
| Size | Medium; length 6-8.5 cm, width 3-5 cm |
| Quantity (number per lateral branch) | 8-10 |
| Shape | Broadly elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Asymmetric |
| Apex | Mucronulate |
| Petiole length | 1-2 cm |
| Petiole diameter | 2 mm |
| Petiole color | Yellow-green 147D |

TABLE 2

| Differences with the comparison variety when grown side-to-side | | |
|---|---|---|
| | 'Zanmudenali' | 'Letitia Time Improved' |
| Inflorescence type | anemone | daisy |
| Ray floret color | White 155D | Green-yellow 1D |

I claim:

1. A new and distinct *chrysanthemum* plant named 'Zanmudenali' as described and illustrated.

* * * * *